United States Patent
Möckli

(10) Patent No.: US 7,060,806 B2
(45) Date of Patent: Jun. 13, 2006

(54) CATIONIC AZO DYE COMPOUND

(75) Inventor: Peter Möckli, Schönenbuch (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 11/007,450

(22) Filed: Dec. 8, 2004

(65) Prior Publication Data

US 2005/0091764 A1    May 5, 2005

Related U.S. Application Data

(62) Division of application No. 10/220,863, filed as application No. PCT/EP01/02316 on Mar. 1, 2001, now Pat. No. 6,843,256.

(30) Foreign Application Priority Data

Mar. 9, 2000    (EP) .................................. 00810197

(51) Int. Cl.
    *C07C 245/00*    (2006.01)
(52) U.S. Cl. .................... 534/560; 534/574; 548/333.1
(58) Field of Classification Search .................... 8/405, 8/406, 409, 570, 573; 548/300, 333.1; 534/560, 534/574
    See application file for complete search history.

(56) References Cited

U.S. PATENT DOCUMENTS 5,708,151 A * 1/1998 Mockli ........................ 534/608
6,843,256 B1 * 1/2005 Mockli ........................ 132/202

FOREIGN PATENT DOCUMENTS

| DE | 1137815 | 10/1962 |
| EP | 0714954 | 6/1996 |
| GB | 885046 | * 12/1961 |
| GB | 910121 | 11/1962 |

OTHER PUBLICATIONS

Chem. Abstr. vol. 60, No. 9, (1964), No. 10828h for Chimia (Switz) 15(1), pp. 163–168 (1961).

* cited by examiner

*Primary Examiner*—Eisa Elhilo
(74) *Attorney, Agent, or Firm*—Kevin T. Mansfield

(57) ABSTRACT

The cationic dyes of formula (1) specified in claim 1 are suitable especially for colouring keratin-containing fibres, more especially for colouring hair.

2 Claims, No Drawings

CATIONIC AZO DYE COMPOUND

This application is a divisional of application Ser. No. 10/220,863, filed Sep. 6, 2002, now U.S. Pat. No. 6,843,256 which is the National Stage of International Application PCT/EP 01/02316, filed Mar. 1, 2001.

The present invention relates to a method of colouring keratin-containing fibres using cationic imidazole dyes, to novel imidazole dyes and to a process for the preparation thereof.

There is already known from EP-A-714 954 a cationic imidazolazo dye that is suitable for colouring hair and is obtained by diazotising 4-alkoxyaniline, coupling with imidazole, then alkylating and quaternising, and finally reacting with p-phenylenediamine. That dye does not however, meet all the demands made in practice of such direct hair dyes, its stability in aqueous solution, in particular, being unsatisfactory.

It has now been found that that disadvantage can be overcome by acylating the free aromatic amino group of such dyes or replacing that group with an alkoxy group. As a result the stability is appreciably improved and the dyes have adequate storage stability also at relatively high pH values, for example at pH values of from 5 to 10, which is of decisive advantage especially for formulations for colouring hair.

The present invention accordingly relates to a method of colouring keratin-containing fibres that comprises treating the fibres with a dye of formula

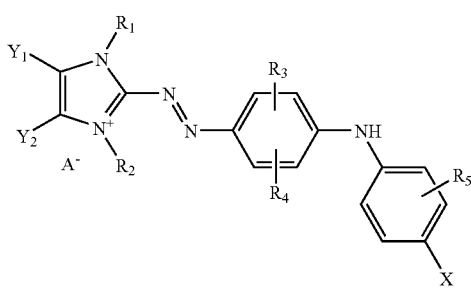

(1)

wherein
$Y_1$ and $Y_2$ are each independently of the other hydrogen, unsubstituted or substituted $C_1$–$C_4$ alkyl, or halogen,
$R_1$ and $R_2$ are each independently of the other hydrogen or unsubstituted or substituted $C_1$–$C_4$alkyl,
$R_3$ and $R_4$ are each independently of the other hydrogen, unsubstituted or substituted $C_1$–$C_4$ alkyl, $C_1$–$C_4$alkoxy or halogen,
$R_5$ is hydrogen, $C_1$–$C_4$alkyl, $C_1$–$C_4$alkoxy or halogen,
X is $C_1$–$C_{12}$alkoxy or a group of formula —N($R_6$)—CO—$R_7$, wherein $R_6$ is hydrogen or $C_1$–$C_4$alkyl and $R_7$ is hydrogen, $C_1$–$C_4$alkyl or —$NH_2$ and
$A^-$ is an anion.

In accordance with the invention, alkyl radicals are to be understood generally as open-chain or branched alkyl radicals, for example methyl, ethyl, n- and iso-propyl and n-, sec- and tert-butyl.

The alkyl radicals may be mono- or poly-substituted, for example by hydroxy, carboxy, halogen, cyano or $C_1$–$C_4$alkoxy.

The alkoxy radicals may contain from 1 to 12 carbon atoms, preferably from 1 to 4 carbon atoms. They are, for example, methoxy, ethoxy, propoxy, isopropoxy, n-butoxy, isobutoxy, tert-butoxy, n-pentyloxy or n-hexyloxy. The alkoxy groups, too, may be substituted, for example by the radicals mentioned as possible substituents for the alkyl groups, especially by hydroxy or $C_1$–$C_4$alkoxy.

There come into consideration as anion $A^-$ both inorganic and organic anions, for example halide, such as chloride, bromide or iodide, sulfate, hydrogen sulfate, methyl sulfate, boron tetrafluoride, aminosulfonate, perchlorate, carbonate, bicarbonate, phosphate, nitrate, benzenesulfonate, formate, acetate, propionate, lactate, and complex anions, such as an anion of a zinc chloride double salt.

The anion is generally governed by the preparation procedure. Preferably, chlorides, hydrogen sulfates, sulfates, methosulfates, phosphates, formates, lactates or acetates are present.

Halogen is to be understood as fluorine, bromine or iodine or, especially, chlorine.

Each of $Y_1$ and $Y_2$ is preferably methyl and especially hydrogen.

Each of $R_1$ and $R_2$ is preferably ethyl, hydroxyethyl or methyl.

$R_3$ and $R_4$ are preferably methoxy, methyl, hydrogen or chlorine.

The preferred meaning of $R_5$ is hydrogen.

X is preferably unsubstituted $C_1$–$C_4$alkoxy or a radical —NH—CO—$R_7$, wherein $R_7$ is especially hydrogen, methyl, ethyl or —$NH_2$.

Special preference is given in accordance with the invention to the use of dyes of formula

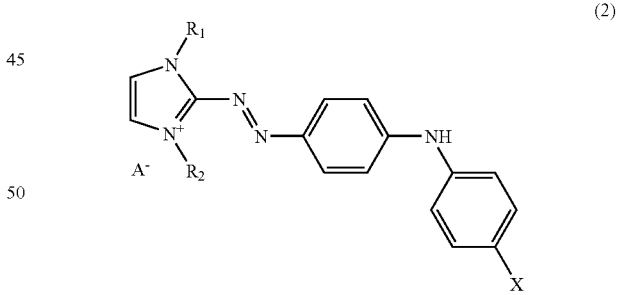

(2)

wherein
$R_1$ and $R_2$ are each methyl or ethyl,
X is unsubstituted $C_1$–$C_4$alkoxy or a radical —NH—CO—$R_7$, wherein $R_7$ is hydrogen, methyl, ethyl or —$NH_2$ and
$A^-$ is an anion.

The dyes of formula (2) are novel and the invention relates also thereto.

The dyes of formulae (1) and (2) are prepared, for example, by acylating the free amino group in a compound of formula

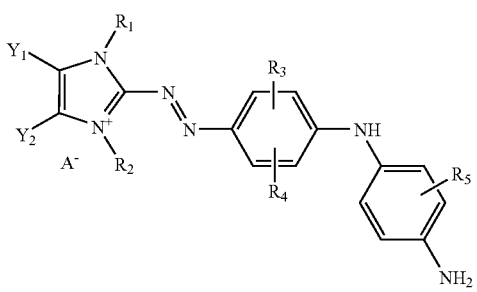

(3)

wherein $Y_1$, $Y_2$, $R_1$, $R_2$, $R_3$, $R_4$, $R_5$ and $A^-$ are as defined for formula (1) per se. This is carried out, for example, by reaction with an appropriate acid, for example formic acid or acetic acid, an anhydride, for example acetic anhydride, or KOCN.

Compounds of formulae (1) and (2) wherein X is an alkoxy group are obtained, for example, by reacting a compound of formula

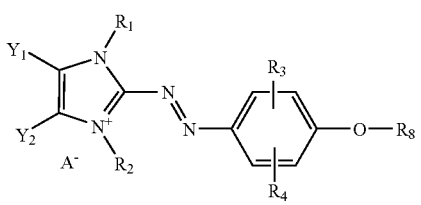

(4)

wherein $Y_1$, $Y_2$, $R_1$, $R_2$, $R_3$ and $R_4$ are as defined for formula (1) and $R_8$ is $C_1$–$C_4$alkyl, with a p-alkoxy-aniline under reaction conditions known per se.

The compounds of formulae (3) and (4) are known or can be obtained in a manner known per se.

The dyes of formulae (1) and (2) are suitable for colouring keratin-containing fibres. "Keratin-containing fibres" are to be understood as wool, furs, feathers and, especially, human hair.

The present invention relates also to compositions comprising such dyes for colouring keratin-containing fibres.

The compounds of formulae (1) and (2) are present in the compositions according to the invention preferably in an amount of from 0.001% to 5%, especially from 0.01% to 1%, based on the total dyeing composition.

The multiplicity of shades and the colour fastness of the dyes of formulae (1) and (2) used in accordance with the invention can be increased by combination with other dyes used in the field of hair-dyeing compositions. They can be combined very readily both with oxidation dyes and with direct dyes, it being possible for the latter to be of cationic nature or also uncharged. Only in the case of anionic direct dyes is a certain degree of caution required, since precipitation may occur in the formulation under certain circumstances.

In all dyeing compositions, the joint use of a plurality of different dyeing substances is also possible; similarly possible is the joint use of a plurality of different oxidation dye precursors from the group of the developer and coupler compounds, for example aromatic compounds having a primary or secondary amino group, nitrogen-containing heterocycles, aromatic hydroxy compounds or amino acids, as described, for example, in German Patent Application 19 717 224.5, especially page 3, line 31 to page 5, line 8.

The dyes of formulae (1) and (2) according to the invention produce colour shades in the range from reddish-violet to violet, and the fastness properties are excellent. Attention is drawn to the property thereof that allows hair that is already dark in colour still to be distinctly altered in shade.

For colouring hair there are preferably used dyes of formula (1) in admixture with one or more further cationic dyes, especially those described in particular on pages 11 to 27 of WO 95/01772. Especially suitable are dye mixtures comprising a dye of formula (1), and also the yellow dye according to Example 1 and/or the red dye according to Example 4 and/or the orange dye according to Example 46 of WO 95/1772.

In a further embodiment, for the purpose of further modification of colour shades the dyeing compositions according to the invention comprise, in addition to the dyes of formula (1) according to the invention, customary direct dyes, for example from the group of the nitroanilines, nitrophenylenediamines, nitroaminophenols, anthraquinones, indophenols, phenazines, phenothiazines, methines or the compounds known as Arianors, such as, for example, the compounds known by the international names or trade names HC Yellow 2, HC Yellow 4, HC Yellow 6, Basic Yellow 57, Basic Yellow 9, Disperse Orange 3, HC Red 3, HC Red BN, Basic Red 76, Basic Red 2, Basic Violet 14, Basic Blue 3, Basic Blue 6, Basic Blue 7, Basic Blue 9, Basic Blue 12, Basic Blue 26, HC Blue 2, HC Blue 7, HC Blue 12, Disperse Blue 3, Basic Blue 99, HC Violet 1, Disperse Violet 1, Disperse Violet 4, Disperse Black 9, Basic Brown 16 und Basic Brown 17, and also picramic acid, 2-amino-6-chloro-4-nitrophenol, 4-amino-2-nitrodiphenylamine-2'-carboxylic acid, 6-nitro-1,2,3,4-tetrahydroquinoxaline, 4-N-ethyl-1,4-bis(2'-hydroxyethylamino)-2-nitrobenzene hydrochloride and 1-methyl-3-nitro-4-(2'-hydroxyethyl)-aminobenzene.

Also very suitable for combination with the dyes according to the invention are cationised nitroaniline and anthraquinone dyes, for example those described in the following patent specifications: U.S. Pat. No. 5,298,029, especially in column 2, line 33 to column 5, line 38; U.S. Pat. No. 5,360,930, especially in column 2, line 38 to column 5, line 49; U.S. Pat. No. 5,169,403, especially in column 2, line 30 to column 5, line 38; U.S. Pat. No. 5,256,823, especially in column 4, line 23 to column 5, line 15; U.S. Pat. No. 5,135,543, especially in column 4, line 24 to column 5, line 16; EP-A-818 193, especially on page 2, line 40 to page 3, line 26; U.S. Pat. No. 5,486,629, especially in column 2, line 34 to column 5, line 29; and EP-A-758 547, especially on page 7, line 48 to page 8, line 19.

Also cationic azo dyes, e.g. according to GB-A-2 319 776, as well as the oxazine dyes described in DE-A-29 912 327 and mixtures thereof with the other direct dyes mentioned therein, can likewise readily be combined.

The compositions of the invention according to this embodiment contain the dyes preferably in an amount of from 0.01 to 5% by weight, based on the total dyeing composition.

In addition, the dyeing compositions according to the invention may also contain naturally occurring dyes, such as, for example, henna red, henna neutral, henna black, camomile blossom, sandalwood, black tea, Rhamnus frangula bark, sage, campeche wood, madder root, catechu, sedre and alkanet root. Such colouring methods are described, for example, in EP-A-404 868, especially page 3, line 55 to page 4, line 9.

In respect of further customary dye components, reference is made expressly to the series "Dermatology", edited by Ch. Culnan, H. Maibach, Verlag Marcel Dekker Inc., New York, Basle, 1986, Vol. 7, Ch. Zviak, The Science of Hair Care, chapter 7, pages 248–250 (direct dyes), and chapter 8, pages 264–267 (oxidation dyes), and to "Europäisches Inventar der Kosmetikrohstoffe", 1996, published by The European Commission, obtainable in diskette form from the Bundesverband der deutschen Industrie-und Handelsunternehmen für Arzneimittel, Reformwaren und Körperpflegemittel e.V., Mannheim.

It is not necessary for the oxidation dye precursors optionally present or for the dyes each to be single compounds, but rather there may be present in the dyeing compositions according to the invention in addition, in lesser amounts, further components associated with the preparation procedures for the individual dyes, provided such components do not have an adverse effect on the dyeing result or do not need to be excluded for other, for example toxicological, reasons.

The dyes of formula (1) according to the invention may also readily be used in combination with other dyes and/or adjuvants used in the colouring of hair, for example with oxidising agents to achieve lightened colouration, as described in WO 97/20545, especially page 9, lines 5 to 9, oxidising agents in the form of permanent-wave fixing solution, as described in DE-A-19 713 698, especially page 4, lines 52 to 55, or EP-A-1 062 940, especially page 6, lines 41 to 47, (and in the equivalent WO 99/40895), oxidation dyeing compositions, as described in EP-A-850 636, especially page 5, line 41 to page 7, line 52, EP-A-850 637, especially page 6, line 50 to page 8, line 44, EP-A-850 638, especially page 7, line 20 to page 9, line 26, and EP-A-852 135, especially page 4, line 54 to page 6, line 53, oxidation dyeing compositions with cationic couplers, as described in WO 99/48856, especially page 9, line 16 to page 13, line 8, and WO 99/48875, especially page 11, line 20 to page 12, line 13, oxidation dyes in the presence of oxidoreductase enzyme, as described in WO 99/17730, especially page 4, line 11 to page 13, line 28, and WO 99/36034, especially pages 3 to 15, autooxidisable oxidation dyes, as described in WO 99/20234, especially page 26, line 16 to page 28, line 15, or nitrobenzene derivatives, as described in WO 99/20235, especially page 26, line 7 to page 30, line 15, polyols or polyethers, as described in EP-A-962 219, especially page 27, lines 14 to 38, thickening polymers, as described in EP-A-970 684, especially page 48, line 16 to page 51, line 4, sugar-containing polymers, as described in EP-A-970 687, especially page 28, line 17 to page 29, line 23, quaternary ammonium salts, as described in WO 00/10517, especially page 44, line 16 to page 46, line 23, anionic surfactants, as described in WO 00/10518, especially page 45, line 11 to page 48, line 3, non-ionic surfactants, as described in WO 00/10519, especially page 45, line 11 to page 50, line 12, or silicones, as described in WO 00/12057, especially page 45, line 9 to page 55, line 2.

The dyeing compositions according to the invention result in intense colourations even at physiologically tolerable temperatures of less than 45° C. They are accordingly suitable especially for colouring human hair. For use on human hair, the dyeing compositions can usually be incorporated into an aqueous cosmetic carrier. Suitable aqueous cosmetic carriers include, for example, creams, emulsions, gels and also surfactant-containing foaming solutions, e.g. shampoos or other preparations, that are suitable for use on keratin-containing fibres. Such forms of use are described in detail in Research Disclosure 42448 (August 1999). If necessary, it is also possible to incorporate the dyeing compositions into anhydrous carriers, as described, for example, in U.S. Pat. No. 3,369,970, especially column 1, line 70 to column 3, line 55. The dyeing compositions according to the invention are also excellently suitable for the colouring method described in DE-A-3 829 870 using a colouring comb or a colouring brush.

The dyeing compositions according to the invention may furthermore comprise any active ingredient, additive or adjuvant known for such preparations. The dyeing compositions in many cases comprise at least one surfactant, there being suitable in principle anionic and also zwitterionic, ampholytic, non-ionic and cationic surfactants. In many cases, however, it has proved advantageous to select the surfactants from anionic, zwitterionic and non-ionic surfactants.

Anionic surfactants suitable for use in the preparations according to the invention include all anionic surface-active substances that are suitable for use on the human body. Such substances are characterised by an anionic group that imparts water solubility, for example a carboxylate, sulfate, sulfonate or phosphate group, and a lipophilic alkyl group having approximately from 10 to 22 carbon atoms. In addition, glycol or polyglycol ether groups, ester, ether and amide groups and also hydroxy groups may be present in the molecule. The following are examples of suitable anionic surfactants, each in the form of sodium, potassium or ammonium salts or mono-, di- or tri-alkanolammonium salts having 2 or 3 carbon atoms in the alkanol group:

linear fatty acids having from 10 to 22 carbon atoms (soaps), ether carboxylic acids of formula R—O—($CH_2$—$CH_2$—O)$_x$—$CH_2$—COOH, in which R is a linear alkyl group having from 10 to 22 carbon atoms and x=0 or from 1 to 16, acyl sarcosides having from 10 to 18 carbon atoms in the acyl group, acyl taurides having from 10 to 18 carbon atoms in the acyl group, acyl isothionates having from 10 to 18 carbon atoms in the acyl group, sulfosuccinic mono- and di-alkyl esters having from 8 to 18 carbon atoms in the alkyl group and sulfosuccinic monoalkylpolyoxyethyl esters having from 8 to 18 carbon atoms in the alkyl group and from 1 to 6 oxyethyl groups, linear alkane sulfonates having from 12 to 18 carbon atoms, linear α-olefin sulfonates having from 12 to 18 carbon atoms, α-sulfo fatty acid methyl esters of fatty acids having from 12 to 18 carbon atoms, alkyl sulfates and alkyl polyglycol ether sulfates of formula R'—O(CH$_2$—CH$_2$—O)$_x$—SO$_3$H, in which R' is a preferably linear alkyl group having from 10 to 18 carbon atoms and x'=0 or from 1 to 12, mixtures of surface-active hydroxysulfonates according to DE-A-3 725 030, especially page 3, lines 40 to 55, sulfated hydroxyalkylpolyethylene and/or hydroxyalkylenepropylene glycol ethers according to DE-A-3 723 354, especially page 4, lines 42 to 62, sulfonates of unsaturated fatty acids having from 12 to 24 carbon atoms and from 1 to 6 double bonds according to DE-A-3 926 344, especially page 2, lines 36 to 54, esters of tartaric acid and citric acid with alcohols which are addition products of approximately from 2 to 15 molecules of ethylene oxide and/or propylene oxide with fatty alcohols having from 8 to 22 carbon atoms.

Preferred anionic surfactants are alkyl sulfates, alkyl polyglycol ether sulfates and ether carboxylic acids having from 10 to 18 carbon atoms in the alkyl group and up to 12 glycol ether groups in the molecule, and also especially salts of saturated and especially unsaturated C$_8$–C$_{22}$carboxylic acids, such as oleic acid, stearic acid, isostearic acid and palmitic acid.

Surface-active compounds that carry at least one quaternary ammonium group and at least one —COO$^{(-)}$ or —SO$^3{(-)}$ group in the molecule are termed zwitterionic surfactants. Zwitterionic surfactants that are especially suitable are the so-called betaines, such as the N-alkyl-N,N-dimethylammonium glycinates, for example cocoalkyldimethylammonium glycinate, N-acylaminopropyl-N,N-dimethylammonium glycinates, for example cocoacylaminopropyl-dimethylammonium glycinate, and 2-alkyl-3-carboxymethyl-3-hydroxyethylimidazolines having from 8 to 18 carbon atoms in the alkyl or acyl group and also cocoacylaminoethylhydroxyethylcarboxymethyl glycinate. A preferred zwitterionic surfactant is the fatty acid amide derivative known by the CTFA name cocamidopropyl betaine.

Ampholytic surfactants are to be understood as meaning surface-active compounds that, in addition to a C$_8$–C$_{18}$-alkyl or -acyl group, contain at least one free amino group and at least one —COOH or —SO$_3$H group in the molecule and are capable of forming internal salts. Examples of suitable ampholytic surfactants include N-alkylglycines, N-alkylpropionic acids, N-alkylaminobutyric acids, N-alkyliminodipropionic acids, N-hydroxyethyl-N-alkylamido-propylglycines, N-alkyltaurines, N-alkylsarcosines, 2-alkylaminopropionic acids and alkylaminoacetic acids, each having approximately from 8 to 18 carbon atoms in the alkyl group. Ampholytic surfactants to which special preference is given are N-cocoalkyl-aminopropionate, cocoacylaminoethylaminopropionate and C$_{12}$–C$_{18}$acylsarcosine.

Non-ionic surfactants contain as the hydrophilic group, for example, a polyol group, a polyalkylene glycol ether group or a combination of polyol and polyglycol ether groups.

Such compounds are, for example:

addition products of from 2 to 30 mol of ethylene oxide and/or from 0 to 5 mol of propylene oxide with linear fatty alcohols having from 8 to 22 carbon atoms, with fatty acids having from 12 to 22 carbon atoms and with alkylphenols having from 8 to 15 carbon atoms in the alkyl group, C$_{12}$–C$_{22}$ fatty acid mono- and di-esters of addition products of from 1 to 30 mol of ethylene oxide with glycerol, C$_8$–C$_{22}$alkyl-mono- and -oligo-glycosides and ethoxylated analogues thereof, addition products of from 5 to 60 mol of ethylene oxide with castor oil and hydrogenated castor oil, addition products of ethylene oxide with sorbitan fatty acid esters, addition products of ethylene oxide with fatty acid alkanolamides.

Examples of cationic surfactants that can be used in the hair-treatment compositions according to the invention are especially quaternary ammonium compounds. Preference is given to ammonium halides, such as alkyltrimethylammonium chlorides, dialkyldimethylammonium chlorides and trialkylmethylammonium chlorides, for example cetyltrimethylammonium chloride, stearyltrimethylammonium chloride, distearyidimethylammonium chloride, lauryldimethylammonium chloride, lauryidimethylbenzylammonium chloride and tricetylmethylammonium chloride. Further cationic surfactants that can be used in accordance with the invention are quaternised protein hydrolysates.

Also suitable in accordance with the invention are cationic silicone oils, such as, for example, the commercially available products Q2-7224 (manufacturer: Dow Corning; a stabilised trimethylsilylamodimethicone), Dow Corning 929 emulsion (comprising a hydroxylamino-modified silicone, which is also referred to as amodimethicone), SM-2059 (manufacturer: General Electric), SLM-55067 (manufacturer: Wacker) and also Abil®-Quat 3270 and 3272 (manufacturer: Th. Goldschmidt; diquaternary polydimethylsiloxanes, quaternium-80).

Alkylamidoamines, especially fatty acid amidoamines, such as the stearylamidopropyldimethylamine obtainable under the name Tego Amid® 18, are distinguished not only by a good conditioning action but also especially by their good biodegradability.

Quaternary ester compounds, so-called "esterquats", such as the methyl hydroxyalkyldialkoyloxyalkylammonium methosulfates marketed under the trade mark Stepantex®, are also very readily biodegradable.

An example of a quaternary sugar derivative that can be used as cationic surfactant is the commercial product Glucquat® 100, according to CTFA nomenclature a "lauryl methyl gluceth-10 hydroxypropyl dimonium chloride".

The alkyl-group-containing compounds used as surfactants may be single substances, but the use of natural raw materials of vegetable or animal origin is generally preferred in the preparation of such substances, with the result that the substance mixtures obtained have different alkyl chain lengths according to the particular starting material used.

The surfactants that are addition products of ethylene and/or propylene oxide with fatty alcohols or derivatives of such addition products may either be products having a "normal" homologue distribution or products having a restricted homologue distribution. "Normal" homologue distribution is to be understood as meaning mixtures of homologues obtained in the reaction of fatty alcohol and alkylene oxide using alkali metals, alkali metal hydroxides or alkali metal alcoholates as catalysts. Restricted homologue distributions, on the other hand, are obtained when, for example, hydrotalcites, alkali metal salts of ether carboxylic acids, alkali metal oxides, hydroxides or alcoholates are used as catalysts. The use of products having restricted homologue distribution may be preferred.

Examples of further active ingredients, adjuvants and additives are as follows:
- non-ionic polymers, for example vinylpyrrolidonelvinyl acrylate copopylmers, polyvinylpyrrolidone and vinylpyrrolidone/vinyl acetate copolymers and polysiloxanes,
- cationic polymers, such as quaternised cellulose ethers, polysiloxanes having quaternary groups, dimethyldiallylammonium chloride polymers, copolymers of dimethyldiallylammonium chloride and acrylic acid, as available commercially under the name Merquat® 280 and the use of which in hair colouring is described, for example, in DE-A-4 421 031, especially page 2, lines 20 to 49, or EP-A-953 334, especially page 27, line 17 to page 30, line 11, acrylamide/dimethyldiallylammonium chloride copolymers, diethyl-sulfate-quaternised dimethylaminoethyl methacrylate/vinylpyrrolidone copolymers, vinylpyrrolidone/imidazolinium methochloride copolymers,
- quaternised polyvinyl alcohol,
- zwitterionic and amphoteric polymers, such as, for example, acrylamidopropyl-trimethylammonium chloride/acrylate copolymers and octylacrylamide/methyl methacrylate/tert-butylaminoethyl methacrylate/2-hydroxypropyl methacrylate copolymers,
- anionic polymers, such as, for example, polyacrylic acids, crosslinked polyacrylic acids, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and acrylic acid/ethyl acrylate/N-tert-butyl acrylamide terpolymers,
- thickeners, such as agar, guar gum, alginates, xanthan gum, gum arabic, karaya gum, locust bean flour, linseed gums, dextrans, cellulose derivatives, e.g. methyl cellulose, hydroxyalkyl cellulose and carboxymethyl cellulose, starch fractions and derivatives, such amylose, amylopectin and dextrins, clays, e.g. bentonite or fully synthetic hydrocolloids such as, for example, polyvinyl alcohol,
- structuring agents, such as glucose and maleic acid,
- hair-conditioning compounds, such as phospholipids, for example soya lecithin, egg lecithin, and cephalins,
- silicone oils, and also conditioning compounds, for example such as those described in DE-A-19 729 080, especially page 2, lines 20 to 49, EP-A-834 303, especially page 2, line 18 to page 3, line 2, or EP-A-312 343, especially page 2, line 59 to page 3, line 11,
- protein hydrolysates, especially elastin, collagen, keratin, milk protein, soya protein and wheat protein hydrolysates, condensation products thereof with fatty acids and also quaternised protein hydrolysates,
- perfume oils, dimethyl isosorbitol and cyclodextrins,
- solubilisers, such as ethanol, isopropanol, ethylene glycol, propylene glycol, glycerol and diethylene glycol,
- anti-dandruff active ingredients, such as piroctones, olamines and zinc Omadine,
- further substances for adjusting the pH value,
- active ingredients such as panthenol, pantothenic acid, allantoin, pyrrolidonecarboxylic acids and salts thereof, plant extracts and vitamins,
- cholesterol,
- light stabilisers and UV absorbers, as described, for example, in EP-A-819 422, especially page 4, lines 34 to 37,
- consistency regulators, such as sugar esters, polyol esters or polyol alkyl ethers,
- fats and waxes, such as spermaceti, beeswax, montan wax, paraffins, fatty alcohols and fatty acid esters,
- fatty alkanolamides,
- polyethylene glycols and polypropylene glycols having a molecular weight of from 150 to 50 000, for example such as those described in EP-A-801 942, especially page 3, lines 44 to 55,
- complexing agents, such as EDTA, NTA and phosphonic acids,
- swelling and penetration substances, such as polyols and polyol ethers, as listed extensively, for example, in EP-A-962 219, especially page 27, lines 18 to 38, for example glycerol, propylene glycol, propylene glycol monoethyl ether, butyl glycol, benzyl alcohol, carbonates, hydrogen carbonates, guanidines, ureas and also primary, secondary and tertiary phosphates, imidazoles, tannins, pyrrole,
- opacifiers, such as latex,
- pearlising agents, such as ethylene glycol mono- and di-stearate,
- propellants, such as propane-butane mixtures, $N_2O$, dimethyl ether, $CO_2$ and air, and also
- antioxidants.

The constituents of the aqueous carrier are used in the preparation of the dyeing compositions according to the invention in the amounts customary for that purpose; for example emulsifiers are used in concentrations of from 0.5 to 30% by weight and thickeners in concentrations of from 0.1 to 25% by weight of the total dyeing composition.

The pH value of the ready-to-use dyeing preparations are usually from 2 to 11, preferably from 5 to 10.

To colour keratin-containing fibres, especially to colour human hair, the dyeing compositions are usually applied to the hair in an amount of from 50 to 100 g in the form of the aqueous cosmetic carrier, left there for approximately 30 minutes and then rinsed off or washed off with a commercially available hair shampoo.

The dyes used according to the invention and the optionally used oxidation dye precursors may be applied to the keratin-containing fibres either simultaneously or in succession, the order in which they are applied being unimportant.

The dyes used according to the invention and the optionally used oxidation dye precursors of the compositions according to the invention may be stored separately or together, either in a liquid to paste-like preparation (aqueous or non-aqueous) or in the form of a dry powder. When the components are stored together in a liquid preparation, the preparation should be substantially anhydrous in order to reduce reaction of the components. When they are stored separately, the reactive components are intimately mixed with one another only immediately before use. In the case of dry storage, before use a defined amount of hot (from 50 to 80° C.) water is usually added and a homogeneous mixure prepared.

The following Examples serve to illustrate the invention without limiting the invention thereto. Unless specified otherwise, parts and percentages relate to weight.

EXAMPLE 1

16 g of the compound of formula

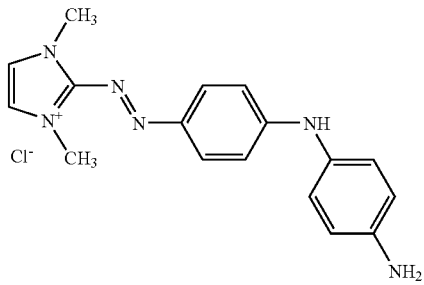

are introduced into 65 g of acetic anhydride and stirring is carried out for 2 hours at a bath temperature of approximately 75° C., after which time all starting material has disappeared. After cooling, filtration is carried out and then washing with acetic anhydride. In order to remove the acetic anhydride, the filter cake is suspended in 200 ml of isopropanol, and the suspension is stirred for 2 hours and filtered again and washed with isopropanol. 17.8 g of the compound of formula

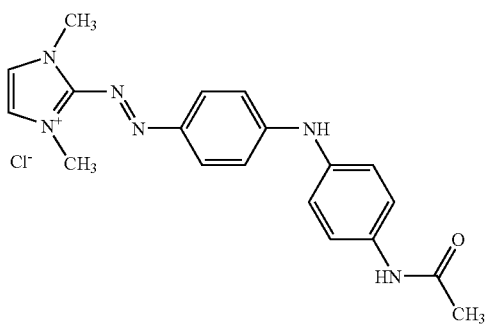

is obtained in very pure form. In aqueous solution, the compound dyes bleached yak hair a brilliant red-tinged violet.

The acetylation can also be carried out in solvents, for example in water:

110 g of the above-described starting compound are suspended in 300 ml of water and, at a temperature of approximately 70° C., a total of 61.4 g of acetic anhydride (=100% excess) are added over a period of one hour. The reaction mixture is cooled with stirring, then filtered and washed with water. After drying, 122.5 g of the acetylated compound are obtained in which only traces of the starting material are still present.

EXAMPLE 2

With stirring, 15 g of the compound of formula

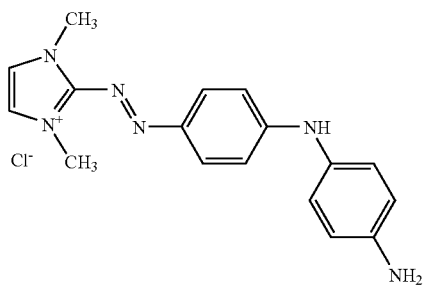

are slowly added to 30 g of formic acid (98%) and heating is carried out for 3 hours at 65° C. 100 ml of isopropanol are added dropwise to the hot solution, which is then stirred until cold.

Filtration followed by thorough washing with isopropanol are carried out. The moist filter cake is first stirred into 65 ml of methanol barely at reflux, and then filtration at 45° C. followed by washing with methanol are carried out. The filter cake is then dissolved hot in 1.5 litres of methanol, the solution is clarified and the mother liquor is concentrated to approximately 85 g using a rotary evaporator, in the course of which there is already partial precipitation of the dye. After cooling suction filtration is carried out, followed by washing with a small amount of methanol and drying. Approximately 9 g of the dye of formula

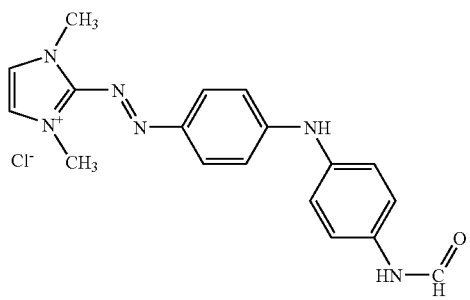

are obtained. In aqueous solution, the dye colours bleached yak hair a brilliant red-tinged violet.

EXAMPLE 3

10.3 g of the compound of formula

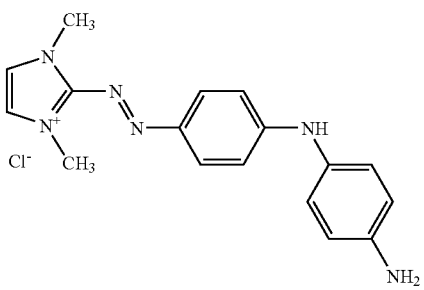

are dissolved in 33 ml of 1N hydrochloric acid in an ice-cooled apparatus. 30 g of ice are added to the reaction solution and then, over a period of half an hour, 2.4 g of potassium cyanate are added in portions. Towards the end a honey-like residue forms, which may sometimes block the stirrer. After standing for from 1 to 2 hours in an ice bath, the residue has turned into a brittle mass that can readily be crushed using a glass rod. The suspension, readily stirrable again, still contains significant amounts of starting material and therefore a further 9 ml of HCl (1N) and 1.2 g of KOCN are added. The ice bath is then removed and filtration at room temperature is carried out. The residue is suspended in water again and stirred at 75° C. for 2 hours. After cooling, filtration and washing with water are carried out.

For purification, the residue is dissolved hot in 12 litres of methanol and the solution is clarified by way of a preheated pressurised suction filter. The filtrate is concentrated to approximately 2 litres using a rotary evaporator, the dye precipitating in pure form. Following cooling, filtration and washing with methanol, 24 g of the dye of formula

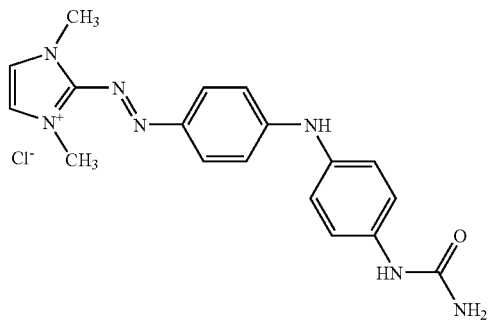

are obtained. In aqueous solution, the dye colours bleached yak hair a brilliant violet, the shade of which is slightly less red-tinged than that of the formyl-substituted dye of Example 2.

EXAMPLE 4

13 g of p-anisidine are dissolved at approximately 50° C. in 45 g of dimethyl-formamide in a suitable stirring apparatus. Then, with stirring, 26.7 g of the compound of formula

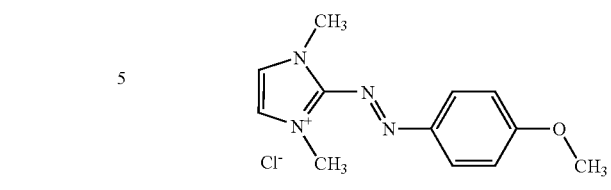

are added in portions and the mixture is stirred for 80 hours at a bath temperature of 90° C. under nitrogen. While still hot, the reaction mixture is diluted with a further 50 g of dimethyl-formamide, allowed to cool slightly and filtered at approximately 40° C. The crystalline filter cake is washed with a further 50 g of DMF in portions, and finally thoroughly suction-filtered dry.

In order to remove small amounts of starting material that are still present, the filter cake is suspended in 80 g of water and stirred for 2 hours at a temperature of from 70 to 75° C. After cooling with stirring, filtration is carried out, followed by washing with a total of 50 g of water, in portions, and drying. 22 g of the dye of formula

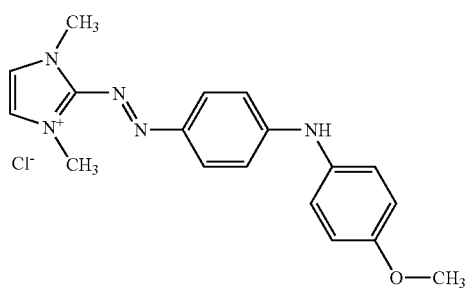

are obtained. In aqueous solution, the dye colours bleached yak hair a brilliant red-tinged violet.

EXAMPLE 5

A 10% solution of a non-ionic surfactant (Plantaren® 2000 [Henkel]) is adjusted to pH 9.5 using citric acid. 0.06% of the dye from Example 1 are dissolved therein. A 1 g strand of undamaged human hair ("Italian white virgin", Imhair Ltd) is treated for 20 minutes at room temperature with 2 g of the dye solution and then rinsed and shampooed. A very attractive violet colouration is obtained, which even after washing eight times can still be seen dearly. The fastness to light of the colouration is excellent.

EXAMPLE 6

A 10% solution of a non-ionic surfactant (Plantaren® 2000 [Henkel]) is adjusted to pH 5.5 using citric acid. The following dyes are dissolved in 100 g of that solution:
0.20 g of the yellow dye according to Example 1 in WO 95/01772
0.05 g of the dye according to the invention from Example 4 of the present Application.

A 1 g strand of undamaged human hair ("Italian white virgin", Imhair Ltd) is treated for 20 minutes at room temperature with 2 g of the above dye solution and then rinsed and shampooed. A very attractive copper colouration having excellent fastness to washing, rubbing and light is obtained.

EXAMPLE 7

A 10% solution of a non-ionic surfactant (Plantaren® 2000 [Henkel]) is adjusted to pH 5.5 using citric acid. The following dyes are dissolved in 100 g of that solution:
0.25 g of the yellow dye according to Example 1 in WO 95/01772
0.08 g of the orange dye according to Example 46 in WO 95/01772
0.06 g of the dye according to the invention from Example 2 of the present Application.
0.11 g of the blue dye according to Example 6 in WO 95/01772.

A strand of bleached human hair is treated for 20 minutes at room temperature with double the amount thereof of the above dyeing solution, and is then rinsed and shampooed once. A black colouration having good fastness to washing and rubbing is obtained.

EXAMPLE 8

The following cationic emulsion base is prepared:
3.8 g of behenic trimonium chloride (Genamin KDM-P [Hoechst])
4.0 g of cetyl alcohol (Lanette 16 [Henkel])
0.5 g of phenoxyethanol (Uniphen P23 [Induchem])
0.1 g of perfume (PÖ Cinque 226482 [drom]) water ad 100
0.06 g of the dye according to Example 4 of the present Application is dissolved in the above base and the pH is adjusted to 6.5 using monoethanolamine. A 1 g strand of undamaged medium-brown human hair (virgin medium-brown hair, Imhair Ltd.) is treated for 20 minutes at room temperature with 2 g of the above dyeing emulsion, and is then rinsed and shampooed once. The hair acquires a very attractive intense aubergine shade having excellent fastness properties.

EXAMPLE 9

A 10% solution of a non-ionic surfactant (Plantaren® 2000 [Henkel]) is adjusted to pH 5.5 using citric acid. The following dyes are dissolved in 100 g of that solution:
0.06 g of the yellow dye according to Example 1 in WO 95/01772
0.09 g of the orange dye according to Example 46 in WO 95/01772
0.03 g of the dye according to the invention from Example 4 of the present Application
0.07 g of the blue dye according to Example 6 in WO 95/01772.

A strand of bleached human hair and a strand of undamaged white human hair are each treated for 20 minutes at room temperature with double the amount thereof of the above dyeing solution, and are then rinsed and shampooed once. In both cases the result is a dark-brown colouration with a distinct, very attractive violet tinge.

EXAMPLE 10

The following dyes are dissolved in 100 g of a solution of a non-ionic surfactant as described in Example 5 (pH 9.5):
0.14 g of Basic Red 76 (Arianor® Madder Red),
0.14 g of the dye according to the invention from Example 4,
0.28 g of Basic Blue 99 (Arianor® Steel Blue),
0.28 g of HC Yellow 2 and
0.14 g of the yellow dye according to Example 1 in WO 95/01772.

A strand of white, undamaged hair is treated for 20 minutes at room temperature with the above solution. The result is a light-brown colouration with an attractive copper tinge.

EXAMPLE 11

The procedure is as in Example 10, except that the dyes specified are replaced by
0.4 g of the red dye according to Example 3 in WO 95/01772 and
0.1 g of the dye according to the invention from Example 4.

The result on the white hair is a very attractive, intensely ruby-red colouration having excellent fastness properties.

What is claimed is:

1. A dye of formula

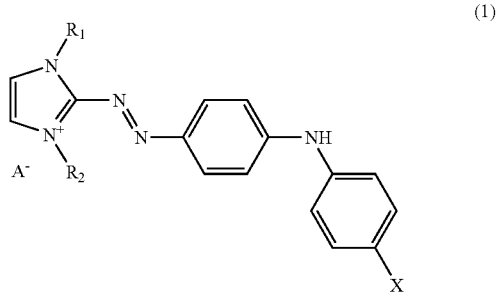

(1)

wherein
$R_1$ and $R_2$ are each methyl or ethyl,
X is unsubstituted $C_1$–$C_4$ alkoxy or a radical —NH—CO—$R_7$, wherein $R_7$ is hydrogen, methyl, ethyl or —$NH_2$, and
$A^-$ is an anion.

2. A dye according to claim 1, wherein $R_1$ and $R_2$ are each methyl, and X is a radical —NH—CO—$R_7$, wherein $R_7$ is hydrogen, methyl or —$NH_2$.

* * * * *